United States Patent [19]

Posner

[11] Patent Number: 5,215,913
[45] Date of Patent: Jun. 1, 1993

[54] IGG-1 HUMAN MONOCLONAL ANTIBODY REACTIVE WITH AN HIV-1 ANTIGEN AND METHODS OF USE

[75] Inventor: Marshall R. Posner, Dedham, Mass.

[73] Assignee: Roger Williams General Hospital, Providence, R.I.

[21] Appl. No.: 485,179

[22] Filed: Feb. 26, 1990

Related U.S. Application Data

[63] Continuation-in-part of Ser. No. 126,594, Nov. 30, 1987.

[51] Int. Cl.$^5$ .................. C12N 5/28; C07K 15/28
[52] U.S. Cl. .................. 530/388.15; 530/388.35; 530/391.3; 530/391.7; 435/240.27
[58] Field of Search .................. 435/240.27; 530/387

[56] References Cited

U.S. PATENT DOCUMENTS

| | | | |
|---|---|---|---|
| 4,574,116 | 3/1986 | Kaplan et al. | 435/70.21 |
| 4,755,457 | 7/1988 | Robert-Guroff et al. | 435/240.2 |
| 4,843,011 | 6/1989 | Sarngadharan et al. | 435/7 |

OTHER PUBLICATIONS

Thali, et al. "Characterization of a Discontinuous Human Immunodeficiency Virus Type 1 gp 120 Epitope Recognized by a Broadly Reactive Neutralizing Human Monoclonal Antibody."
Journal of Virology, vol. 65, No. 11, pp. 6188–6193, Nov. 1991.
McMichael, et al. (Eds.) Monoclonal Antibodies in Clinical Medicine Chapters 7 and 24. Academic Press, Inc. New York 1982.
Matsushita, et al. Human Monoclonal Antibody Directed Against an Envelope Glyco Protein of Human T–Cell Leukemia Virus . . . Proc. Natl. Acad. Sci. USA vol. 83 pp. 2672–2676 1986.

Primary Examiner—John J. Doll
Assistant Examiner—George C. Elliott
Attorney, Agent, or Firm—John P. White

[57] ABSTRACT

The present invention provides a human-mouse myeloma analog, designated HMMA 2.11TG/O, which has been deposited with the American Type Culture Collection (ATCC) under Accession Number HB 9583. The invention also provides a hybridoma designated F 105, which also has been deposited with the ATCC under Accession Number HB 10363.

The invention also concerns a monoclonal antibody-producing hybridoma produced by the fusion of the human-mouse myeloma analog and an antibody-producing cell. Other embodiments of the invention provide a method for producing a monoclonal antibody-producing hybridoma which comprises fusing the human-mouse myeloma analog with a human antibody-producing cell and a therapeutic method for treating a subject having a pathogen- or tumor-related disease which comprises administering to the subject a monoclonal antibody specific for the disease produced by the monoclonal antibody-producing hybridoma. In addition, a method of blocking binding of the human immunodeficiency virus and method of preventing infection of human cells by the human immunodeficiency virus are disclosed, as well as methods of detecting the virus or its antigen.

4 Claims, 8 Drawing Sheets

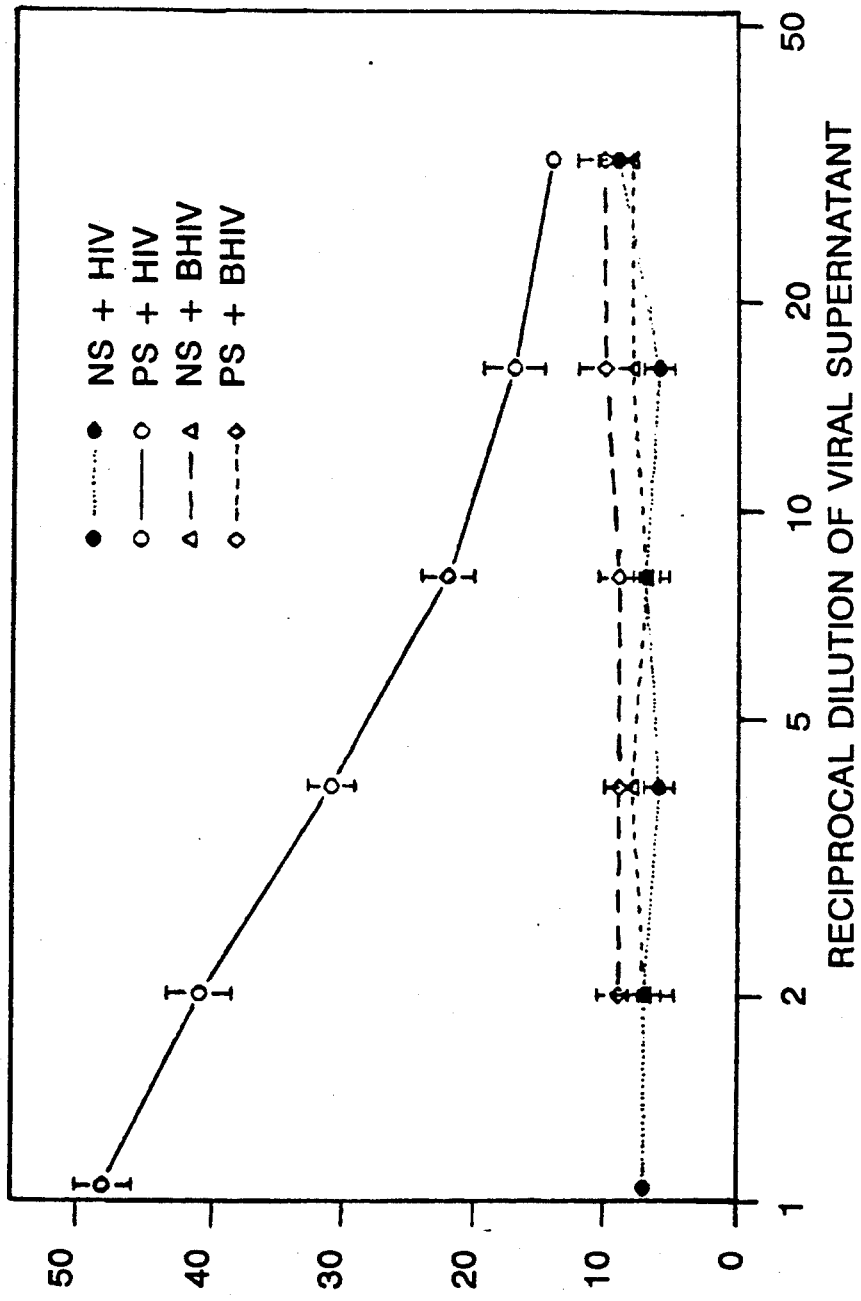

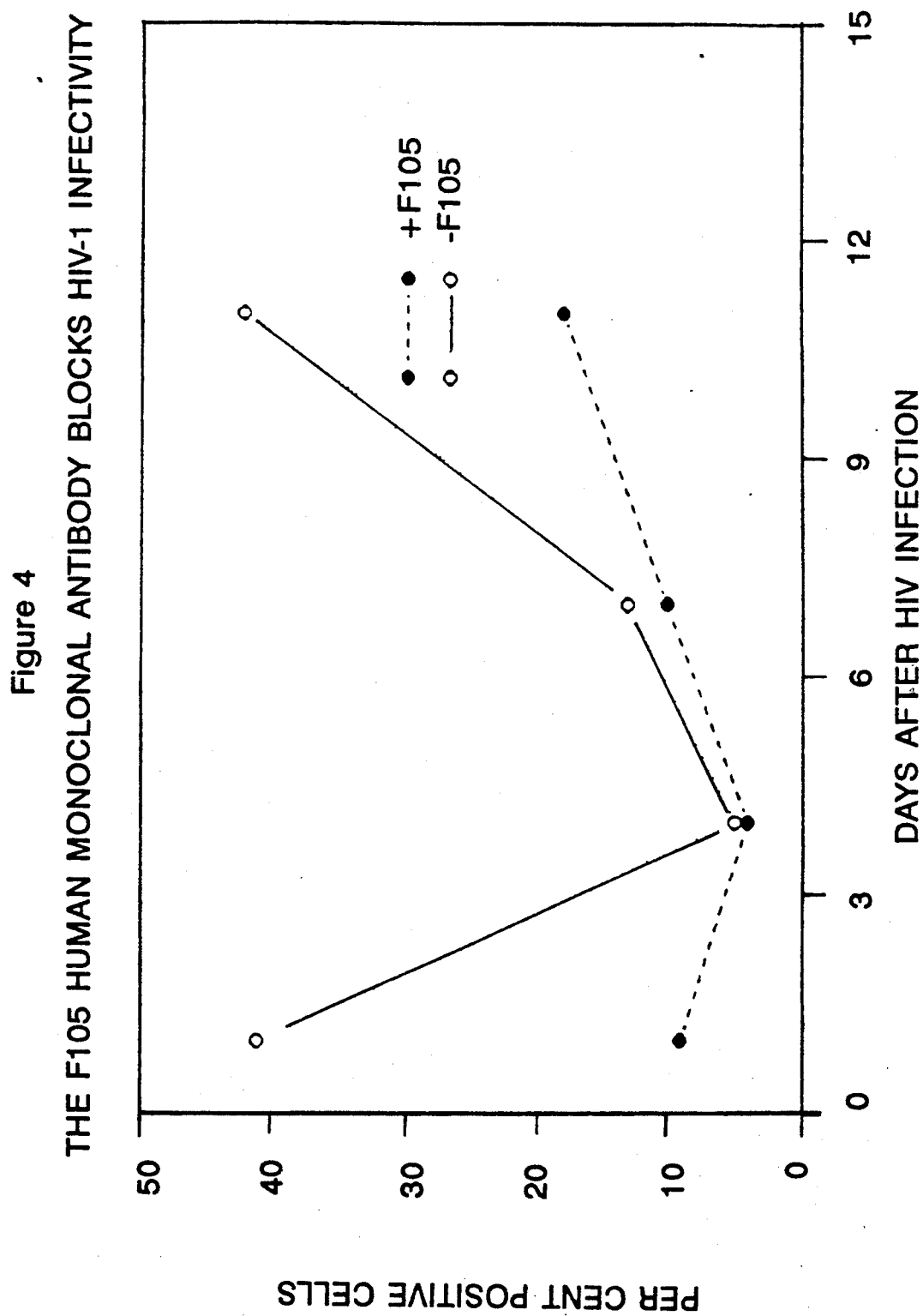

IGG-1 HUMAN MONOCLONAL ANTIBODY REACTIVE WITH AN HIV-1 ANTIGEN AND METHODS OF USE

The invention described herein was made in the course of work under Grant No. R01 CA 38687 from the National Cancer Institute, National Institutes of Health, U.S. Department of Health and Human Services and Grant No. R01-AI 26926 from the National Institute of Health. The United States Government has certain rights in this invention.

This application is a continuation-in-part application of U.S. Ser. No. 126,594, filed Nov. 30, 1987, the contents of which are incorporated herein by reference.

BACKGROUND OF THE INVENTION

Throughout this application various publications are referenced by Arabic numerals. Full citations for these references may be found at the end of the specification immediately preceding the claims. The disclosures of these publications in their entireties are hereby incorporated by reference into this application in order to more fully describe the state of the art to which this invention pertains.

The routine production of human monoclonal antibodies has been of interest since the construction of murine hybridomas which secrete murine monoclonal antibodies of predetermined specificity were originally described (1).

While murine monoclonal antibodies provide valuable tools for the study of biological processes, major limitations are apparent. First, there are restricted number of antigens recognized by these antibodies (50). For example, antibodies directed to polymorphic determinants of the HLA and DR antigens have been difficult to identify (51). Moreover, it has been almost impossible to identify specific human tumor-associated antigens (51-57). Secondly, the pathogenesis of the autoimmune phenomenon in diseases such as diabetes require that the human autoantibodies be defined (58). Finally, therapeutics using murine monoclonal antibodies are restricted due to the formation of antimurine antibodies by the patients receiving the murine monoclonal antibodies for treatment (59-62). It is therefore likely that human monoclonal antibodies will provide major tools for the study of human neoplasia (9-14), autoimmune diseases (2-8), and infectious diseases (16-20), and will serve as potential therapeutic and diagnostic agents for these and other illnesses.

To date, Epstein-Barr Virus (EBV) transformation of antibody-producing human B cells, selection of myeloma serum proteins, and fusion of both murine and human myeloma cell lines or analogs with antibody-producing cells have served as the only practical methods for obtaining human monoclonal antibodies. These methods, however, lack one or more of the features which have made the routine production of murine monoclonal antibodies useful (21-26). While myeloma serum proteins have been used by some investigators as sources of antibodies, this method is dependent upon the large scale screening of rare patients. Lack of reproducibility and continual production, as well as restricted antigen specificities, limit the applicability of this method. EBV virus transformation of antibody-producing B cells has provided the major source of human monoclonal antibodies reported in the literature. There are numerous inherent and methodological problems associated with the use of EBV transformation as a technique for producing antibodies. First and foremost is the instability of monoclonal antibody production by these cell lines (21). Because they have an extremely poor cloning efficiency and unstable antibody secretion, only a few human monoclonal antibody-secreting cell lines have been maintained and have produced sufficient quantities of antibody for use in subsequent studies (3, 11). Moreover, the low frequency and lack of specificity of EBV transformation has necessitated selection methods designed to enhance the recovery and transformation of antibody-secreting B cells (21, 29, 30).

The development of human monoclonal antibodies by fusion of myeloma cell lines or analogs with antibody-producing cells has been slowed by two major factors: 1) lack of an appropriate human fusion partner and 2) insufficiently available antigen-specific, human B cells. The presently available human fusion partners are lacking in important characteristics necessary for the production of monoclonal antibodies, i.e., efficient fusion, easy clonability of cell lines and fusion-resulting hybrids, and continuous secretion of large quantities of antibody by the hybrids. Without these characteristics, which are important features of murine fusion partners, it will be extremely difficult to obtain human monoclonal antibodies to many antigens. Human myeloma or lymphoblastoid cell lines have been used for fusion, but frequently these have either a low fusion efficiency, poor growth and cloning, or unstable secretion by the resulting hybrids (6, 23, 31-33). For example, NSI, a murine myeloma cell line, fuses with an efficiency of 1/10,000 with mouse spleen cells (66). Comparative fusion efficiency of LiCron HMY-2, SK007, UC729-6 or GM 1500 is between 1/500,000 and 1/1,000,000 with human cells (6, 33, 67, 68). In addition, several of these cell lines, including derivatives of UC729-6 and LTR228, fuse poorly with normal peripheral blood mononuclear cells (PBM). High fusion efficiency is particularly important in a human system because of the relative rarity of antibody-producing B cells, even in individuals undergoing programmed immunization. In optimally tetanus immunized volunteers, as few as 1 out of 10,000 circulating B cells secrete antitetanus antibody (38). Since B cells represent less than 10% of circulating PBM, large numbers would be needed to obtain a single antibody-secreting hybrid. Direct comparisons of a number of human myeloma cell lines, mouse myeloma cell lines, and human lymphoblastoid cell lines as human fusion partners have generally indicated fusion efficiencies on the order of $1/10^5$–$10^6$ cells, with poor stability, and secretion between 100 ng and 10 μgm/ml in routine cultures (6, 23, 31).

As an alternative to presently available human and murine cell lines used as fusion partners, a number of investigators have attempted to construct myeloma analogs that might be superior for human monoclonal antibody production. Murine hybridization experiments have shown that fusions between B cells with undifferentiated characteristics and B cells with more differentiated characteristics result in the promotion of those differentiated characteristics in the hybrids (43, 44). Thus, Laskow, et al., and others, were able to promote the appearance of phenotypic characteristics of a more differentiated B cell, specifically including intact immunoglobulin production or secretion, by fusing undifferentiated B cells with a myeloma cell line (43-46). In the attempts to construct a human myeloma analog that would retain the desirable characteristics in the human fusion partner, it was theorized that the appropriate selection of cells for hybridization would result in the sequential improvement of a series of constructed myeloma analogs (25, 26). These human myeloma analogs were constructed by the fusion of a non-secreting human myeloma cell line with a variety of human cells at selected stages of differentiation. In these studies, while fusion efficiency was high and growth characteristics were excellent, stable secretion of monoclonal immunoglobulin was obtained only from fusions with established malignant human cell lines already committed to secretion. Antibody secretion was rapidly lost by the cloned hybridomas. It is possible that the choice of the non-secreting human myeloma cell line as the basis for the series of constructed human myeloma analogs may have had an impact on the ability of subsequently generated human myeloma analogs and hybridomas to support stable antibody production.

As an alternative to analogs formed by the fusion of human myeloma cells with human cells, heterohybridomas have been constructed by the fusion of murine myeloma cells with human cells (34–37). Some investigators, including the present inventor, have constructed human-mouse myeloma analogs by fusing murine myelomas with a variety of human cells. The murine myelomas used for fusion derive principally from the MOPC21 cell line, developed by Potter and associates and adapted to in vitro growth by Horibata and Harris. (27, 28, 39). This cell line and derivatives thereof are routinely used in the production of murine monoclonal antibodies as the fusion partner. Teng, et al., fused MOPC21 with the human cell line SK007 (34), Ostberg and Pursch fused it with a human B lymphocyte (37), and Foung, et al. fused normal peripheral blood lymphocytes with a derivative of SP2, a murine myeloma hybrid (35). Carroll, et al., compared a number of these human-mouse myeloma analogs for fusion efficiency, immunoglobulin secretion and stability (36). A heterohybridoma, K6H6/B5, constructed by fusion with NSI and human B lymphoma cells, was found to be superior to the other human-mouse myeloma analogs. This heterohybridoma has a fusion efficiency of $1/10^5$ cells with 60% of the hybridomas secreting immunoglobulins. Immunoglobulin secretion by the hybrids was on the order of 2–3 $\mu$gm/ml.

Despite this effort, most heterohybridoma analogs have proven to have unstable secretion (25, 26) or a poor fusion efficiency when compared to murine myeloma cell lines. Since specific human antibody-producing cells are rare in the peripheral blood, a higher fusion efficiency is a desirable feature of a human fusion partner (38).

The present invention provides a new human-mouse myeloma analog, which has been termed HMMA 2.11TG/0, a method of constructing it and a method of routinely using the human-mouse myeloma analog for the production of human monoclonal antibodies. The HMMA 2.11TG/O cell line has an extremely high fusion efficiency with normal PBM and EBV transformed PBM. It clones readily and, once cloned, stably secretes large amounts of human monoclonal antibody.

Human Immunodeficiency Virus 1 (HIV-1) infection represents a new and extremely serious health threat. The evolving epidemic has spread to numerous risk groups in this country and new related viruses have now appeared in Africa and other geographical areas (69–73). Patients with HIV-1 infection may develop a variety of directly related illnesses, including frank Acquired Immunodeficiency Syndrome (AIDS), AIDS Related Complex (ARC), encephalopathy, and AIDS related malignancies. These complications of HIV-1 infection are thought to derive in large part from a progressive and profound immunosuppression which occurs during the course of the illness, or to associated, possible, direct effects of the virus on specific organs, such as the brain (69–73). At the present time it is not known which patients infected with HIV-1 will go on to manifest increasingly serious and morbid complications of the disease, and why some, but not all, individuals will undergo this progression. It is felt that a profound depression of cellular immunity, as a manifestation of viral mediated destruction of T cells, may be involved in this process. Inversion of the normal T4/T8 ratio, depletion of lymphocytes bearing the CD4 antigen, and lymphopenia in infected individuals are strongly correlated with progression to AIDS (74, 75). The preferential infection of T4 lymphocytes, syncytia formation and death of infected T4 cells, and the ability of some antibodies directed at the CD4 complex to prevent infection of cells by HIV-1, have implicated this population of T cells and the CD4 complex in the pathogenesis of this disease (72, 76–79).

While studies of immunodepression in this disease have concentrated on the cellular arm of the immune response, the humoral immune system has also been profoundly effected by HIV-1 infection. Patients infected with HIV-1 have diminished responses to immunization with potent immunogens such as Keyhole Limpet Hemocyanin and Hepatitis B vaccines (80–82). Paradoxically patients also have serum hypergammaglobulinemia, possibly as a result of chronic, non-specific, B cell stimulation. Several pieces of evidence support this contention. Isolated B cells from infected individuals are more likely to spontaneously secrete immunoglobulins as well as specific antibodies, including antibodies to HIV-1 (80–82). These circulating B cells also appear activated on the basis of cell surface phenotypic changes (83). In addition, circulating B cells from HIV-1 infected patients are less likely to be transformed by exogenously added Epstein Barr Virus (EBV), although spontaneous outgrowth of EBV transformed B cells is higher than that seen in normals (82). Because EBV transformation preferentially occurs in non-activated B cells, these data support the notion that circulating B cells are chronically activated (84). Taken together, these studies demonstrate that alteration of the humoral immune response is a major occurrence in HIV-1 infection. The importance of the humoral immune response to HIV-1 in the in vivo control of the disease is controversial. Some epidemiologic studies of risk groups have suggested that the presence of serum antibody reactive with the gp120 envelope protein of the HIV-1 virus, and capable of neutralizing virus in infection assays, is correlated with lack of disease progression (85–87). Longitudinal studies of thalassemic patients, infected via frequent blood transfusion, and of patients infected during treatment for curable malignancies support the notion that neutralizing antibodies play a role in preventing the development of AIDS (85, 87). Conflicting evidence has also been presented to suggest that these antibodies may have little role in preventing Kaposi's Sarcoma, a manifestation of HIV-1 infection (88, 89). At least one report has suggested that serum antibodies capable of blocking reverse transcriptase activity are also correlated with continued lack of disease progression (90). While the presence of neutralizing antibodies, and antibodies inhibiting reverse transcriptase activity, may be important in the in vivo control of this disease, they may also represent epiphenomena of HIV-1 infection and their presence or absence may be unrelated to the direct cause of further immunosuppression. This might pertain if, for example, viral infection occurred via cell-cell interactions (91). Alternatively, genetic variation or drift in viral envelope proteins may lead to escape from humoral immune control, although some epidemiologic studies have suggested that epitopes involved in viral binding and neutralization are frequently conserved across isolates (92-95). A third mechanism for escape from control might involve dysregulation of the humoral immune system leading to down regulation of antibody synthesis through the destruction of the CD4 lymphocyte population (74, 82). It might be speculated that this process could involve production of anti-idiotypic antibodies some of which may bind to T cells and contribute further to immunosuppression (96, 97). Thus, despite the tentative, speculative, and conflicting data regarding the humoral immune response to HIV-1, it is of great importance that the relationship of the antibody response to HIV-1 and progression of the disease be understood since there remains a real likelihood that this response may significantly alter the course of infection.

Murine monoclonal antibodies reactive with either the CD4 complex or HIV-1 envelope proteins are capable of inhibiting infectivity of HIV-1 in in vitro systems (77-79). These monoclonal antibodies are being used to study idiotypic responses, CD4 attachment, and antigen binding sites on HIV-1 related proteins. For example, a murine monoclonal anti-idiotypic antibody, but not polyclonal rabbit anti-idiotypes, reactive with CD4 binding murine monoclonals reacts with HIV-1 envelope proteins and inhibits cellular infection (79).

Despite the obvious utility of many of these antibodies and their availability for study, the precise determinants involved in the human humoral immune response remain unknown. In order to study both the human humoral response to HIV-1 infection, and the regulation of this response, it is important to obtain the human equivalent of the currently available murine monoclonal antibodies. Human monoclonal antibodies to HIV-1 provide a series of uniform reagents that would be useful in determining the precise epitopes involved in the immune response to this virus, the idiotypic restrictions in the humoral immune response, and the potentially important impact of anti-idiotypic regulation. Moreover, human monoclonal antibodies serve as useful diagnostic and therapeutic reagents in the evaluation and treatment of the disease. Therapeutic advantages of human monoclonal antibodies over murine monoclonal antibodies include a decreased potential for direct immunization against the antibodies (98). In addition, anti-idiotypic antibodies binding to populations of normal T cells prove useful in studying the human immune response in general (99).

SUMMARY OF THE INVENTION

The present invention provides a human-mouse myeloma analog, designated HMMA 2.11TG/O, which has been deposited with the American Type Culture Collection (ATCC) under Accession Number HB 9583. The invention also concerns a monoclonal antibody-producing hybridoma produced by the fusion of the human-mouse myeloma analog and an antibody-producing cell. Other embodiments of the invention provide a method for producing a monoclonal antibody-producing hybridoma which comprises fusing the human-mouse myeloma analog with a human antibody-producing cell and a therapeutic method for treating a subject having a pathogen- or tumor-related disease which comprises administering to the subject a monoclonal antibody specific for the disease produced by the monoclonal antibody-producing hybridoma.

The invention provides a hybridoma deposited with the American Type Culture Collection (ATCC) under Accession No. HB10363 and designated F 105 and the human monoclonal antibody which it produces. The invention also concerns an anti-idiotypic antibody directed against this monoclonal antibody and methods of use.

This invention also provides a human monoclonal antibody directed to an epitope on human immunodeficiency virus (HIV) and capable of blocking the binding of HIV to human cells and capable of preventing infection of human cells by HIV.

BRIEF DESCRIPTION OF THE FIGURES

FIG. 3: Shows the effect of human monoclonal antibody F 105 on viral binding to HIV 3b infected HT-H9 cells.

FIG. 4: Shows that the F 105 human monoclonal antibody blocks HIV-1 infectivity.

DETAILED DESCRIPTION OF THE INVENTION

Figure 1A:
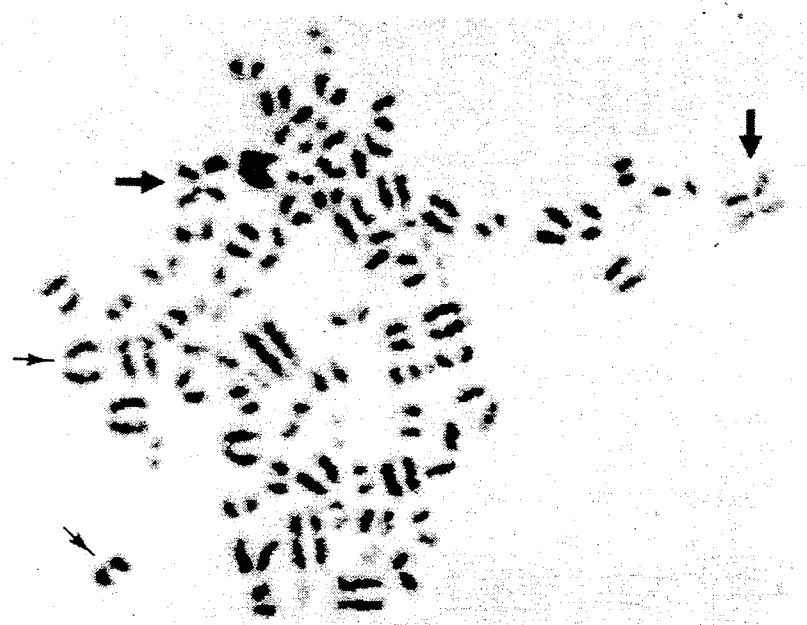
FIGS. 1A and 1B: Representative photomicrographs of chromosome preparations from the HMMA 2.11TG/O cell line (1A); and two cloned antibody secreting hybridomas, F3D$_1$, 2F$_6$(1B); and F5B$_6$A$_6$(1C).

The present invention provides a human-mouse myeloma analog designated HMMA 2.11TG/O which has been deposited with the American Type Culture Collection (ATCC) Rockville, Md., U.S.A. 20852 under Accession Number HB 9583 pursuant to the requirements of the Budapest Treaty on the International Recognition of the Deposit of Microorganisms for the Purposes of Patent Procedure (Budapest Treaty).

The human-mouse myeloma analog of the present invention comprises hybrid human-murine karyotypes and cell surface phenotypes and is produced by the fusion of a mouse myeloma cell derived from MOPC21 and a human bone marrow mononuclear cell. The mouse myeloma cell belongs to the mouse myeloma cell line designated P3×63Ag8.653, a non-secreting murine myeloma cell line which is a mutant derivative of the cell line MOPC21. The human bone marrow mononuclear cell (BMMC) is obtained from humans with a IgA/Kappa myeloma. The human donors are heavily treated with chemotherapeutic agents and are uremic and anemic prior to the obtaining of the BMMC by aspiration.

The analog resulting from the fusion of the BMMC and the mouse myeloma cell is grown in the presence of thioguanine (particularly 6-thioguanine) and ouabain and thus, is resistant to both ouabain and thioguanine. The resulting analog is also sensitive to mixtures of hypoxanthine, aminopterin, and thymidine (HAT).

Another aspect of the present invention provides a monoclonal antibody-producing hybridoma produced by the fusion of the human-mouse myeloma analog and a human antibody-producing cell. In the preferred embodiments, the antibody-producing cell is a human peripheral blood mononuclear cell (PBM), a mitogen stimulated PBM such as a Pokeweed Mitogen (PMW) or a phytohemagglutinin stimulated normal PBM (PHA(S)), or an Epstein-Barr Virus (EBV) transformed B cell. The human-mouse myeloma analog described above has an average fusion efficiency for growth of antibody-secreting hybridomas of greater than 1 out of 25,000 fused cells when fused with human PBM, mitogen stimulated PBM and EBV transformed B cells. Especially useful antibody-producing hybridomas of the present invention are those hybridomas which produce monoclonal antibodies specific for human myelomonocytic leukemia, human acute lymphoblastic leukemia, human immunodeficiency virus (HIV), or human colon carcinoma.

This invention further provides a human monoclonal antibody directed to an epitope on human immunodeficiency virus (HIV) and capable of blocking the binding of HIV to human cells and capable preventing infection of human cells by HIV. In one embodiment of the invention, the epitope recognized by the human monoclonal antibody is the epitope recognized by a monoclonal antibody designated F 105. This invention also provides the human monoclonal antibody F 105. Monoclonal antibody F 105 is produced by a hybridoma also designated F 105 which has been deposited with the American Type Culture Collection (ATCC) Rockville, Md., U.S.A. 20852 under Accession Number HB10363 pursuant to the requirements of the Budapest Treaty on the International Recognition of the Deposit of Microorganisms for the Purposes of Patent Procedure (Budapest Treaty).

Monoclonal antibody F 105 may be labelled with a detectable marker. Detectable markers useful in the practice of this invention are well known to those of ordinary skill in the art and may be, but are not limited to radioisotopes, dyes or enzymes such as peroxidase or alkaline phosphatase. In addition, human monoclonal antibody F 105 may be conjugated with a cytotoxic agent.

This invention also concerns an anti-idiotypic antibody directed against the human monoclonal antibody F 105. This anti-idiotypic antibody may also be labelled with a detectable marker. Suitable detectable markers are well known to those of ordinary skill in the art and may be, but are not limited to radioisotopes, dyes or enzymes such as peroxidase or alkaline phosphatase.

The anti-idiotypic antibody directed against human monoclonal antibody F 105 is produced when an animal is injected with the F 105 antibody. The animal will then produce antibodies directed against the idiotypic determinants of the injected F 105 antibody (100).

Alternatively, the anti-idiotypic antibody directed against the human monoclonal antibody F 105 is produced by contacting lymphoid cells of an animal with an effective-antibody raising amount of the antigen F 105; collecting the resulting lymphoid cells; fusing the collected lymphoid cells with myeloma cells to produce a series of hybridoma cells, each of which produces a monoclonal antibody; screening the series of hybridoma cells to identify those which secrete a monoclonal antibody capable of binding to the F 105 human monoclonal antibody; culturing the resulting hybridoma cell so identified and separately recovering the anti-idiotypic antibody produced by this cell (101). Animals which may be used for the production of anti-idiotypic antibodies in either of the two above-identified methods include, but are not limited to humans, primates, mice, rats, or rabbits.

The invention also concerns a method for producing a monoclonal antibody-producing hybridoma which comprises fusing the human-mouse analog with an antibody-producing cell, especially those antibody-producing cells listed hereinabove, and the monoclonal antibody which said hybridoma produces.

Another embodiment of the invention is a therapeutic method for treating a subject having a pathogen- or tumor-related disease which comprises administering to the subject a monoclonal antibody specific for the disease produced by the monoclonal antibody-producing hybridoma, wherein the monoclonal antibody is capable of curing the disease or of alleviating its symptoms. Preferably, the pathogen- or tumor-related disease is myelogenous leukemia, acute lymphoblastic leukemia, colon carcinoma, acquired immunodeficiency syndrome, or human immunodeficiency viral infection. The human-mouse myeloma analog of the present invention and the monoclonal antibody-producing hybridomas produced therefrom are also useful as research and diagnostic tools for the study of these diseases.

The invention further concerns a method of blocking binding of the human immunodeficiency virus (HIV) to human cells and a method of preventing infection of human cells by HIV which comprises contacting HIV with an amount of the human monoclonal antibody directed to an epitope on HIV, effective to block binding of HIV to human cells and preventing infection of human cells by HIV.

A method of detecting in a sample the presence of HIV also is disclosed which comprises contacting a suitable sample with the monoclonal antibody F 105 so as to form an antibody-antigen complex between the monoclonal antibody and any HIV present in the sample and detecting the presence of any complex so formed, thereby detecting in the sample the presence of HIV. In one embodiment, the human monoclonal antibody F 105 is labelled with a detectable marker. Suitable samples which are useful in this method are, but are not limited to biological fluids from a human subject such as blood, serum, plasma, urine, nasal mucosal discharge, oral mucosal discharge, vaginal mucosal discharge, anal mucosal discharge and serosal fluids.

The method of detecting anti-HIV antibody also is provided by the invention. The method comprises contacting a suitable sample with the anti-idiotypic antibody described hereinabove so as to form an anti-idiotypic antibody-anti-antibody complex between the anti-idiotypic antibody and any anti-HIV antibody in the sample and detecting the presence of any complex so formed, thereby detecting in the sample the presence of anti-HIV antibody. In one embodiment, the anti-idiotypic antibody is labelled with a detectable marker. Suitable samples which are useful in this method are, but are not limited to, biological fluids from a human subject such as blood, serum, plasma, urine, nasal mucosal discharge, oral mucosal discharge, vaginal mucosal discharge, anal mucosal discharge and serosal fluids.

A vaccine against human immunodeficiency virus (HIV) also is provided which comprises a human anti-idiotypic antibody described hereinabove in an amount effective to prevent HIV infection and a pharmaceutically acceptable carrier.

The invention further provides the DNA sequences which encodes for the variable regions of the human monoclonal antibody F 105. The DNA sequences are isolated by first isolating and purifying the mRNAs which encode for the F 105 heavy and light chain. cDNA copies are then made from these purified mRNAs to thereby provide the DNA sequences which encode for the variable regions.

The present invention is further illustrated in the Experimental Details, Results and Discussion sections which follow. These sections are set forth to aid in an understanding of the invention but are not intended to, and should not be constructed to, limit in any way the invention as set forth in the claims which follow thereafter.

Experimental Details

Cell Culture

Cell lines and established hybridomas were grown in AlphaMEM, lacking nucleosides with the following additives: 1 mM sodium pyruvate, 2 mM 1-glutamine, 1% (v/v) non-essential amino acids, 10% (v/v) fetal bovine serum (high cloning efficiency and growth promotion; GIBCO (Grand Island, N.Y.), 0.22% (w/v) sodium bicarbonate, and 50 $\mu$gm/ml gentamycin. All other cell cultures were performed with the same media containing 20% fetal bovine serum. Other additives were included as indicated. Cultures growing in flasks were sealed and maintained at 37° C. after gassing with a 5% $CO_2$/air (v/v) mixture. Repeated gassings after initiation were performed as needed. Cultures in microtiter plates or multiwells were incubated in a 5% $CO_2$ atmosphere at 37° C. in a humidified incubator.

Cell Lines

The P3×63Ag8.653 cell line, a non-secreting murine myeloma cell line (39), was used for human-murine fusions (supplied by Dr. A. R. Frackelton). The B95-8 marmoset cell line (40) was used as a source of EBV for cell transformation (supplied by Dr. H. Lazarus).

Volunteer and Patient Cells

PBM and BMMC were obtained by venipuncture or bone marrow aspiration, respectively, in preservative free heparin (O'Neal, Jones and Feldman; St. Louis, Mo.), and separated from contaminating cells by density gradient separation as previously described (25, 26). If not used immediately, cells were stored by cryopreservation in liquid nitrogen after resuspension in media containing 10% dimethylsulfoxide. PBM from volunteers were obtained after immunization with tetanus toxoid at varying time intervals.

Cell Fusion

Fusions were performed using a prepared 46% (w/v) solution of polyethylene glycol (PEG) 8000 (JT Baker Chemical Co., Phillipsberg, N.J.) in Puck's Saline G without calcium or magnesium (PSG/WO) (25). PEG was autoclaved at 121° C. for 15 minutes and immediately mixed with PSG/WO warmed to 37° C. Sterile 1M sodium hydroxide was used to adjust the pH to 8.0 and 4 ml aliquots were stored sterilely at 4° C., in glass vials, protected from light. The myeloma or myeloma analog was fused in a ratio of 2:1 with the other parental cells. Cells to be fused were pooled and washed twice with PSG/WO in a 50 ml polypropylene centrifuge tube. After the final wash, the PSG/WO was decanted, the cell pellet was resuspended in the residual PSG/WO, and 1.5 ml of PEG solution, previously warmed to 37° C., was slowly added, dropwise to the pellet with frequent gentle mixing. The cells were allowed to incubate for 1 minute and warm PSG/WO was added, dropwise to the pellet with frequent mixing. The first 1.0 ml was added over 1 minute, the second and third over 30 seconds each. Subsequently, a total of 20 ml was added to the centrifuge tube. The cells were centrifuged at 400×G for 10 minutes, the PEG solution was decanted, and the cells were resuspended in culture media with hypoxanthine ($1\times10^{-4}$M), aminopterin ($4\times10^{-7}$M), and thymidine ($1.6\times10^{-5}$M) (HAT), (SIGMA, St. Louis, Mo.).

Fused cells were distributed in 96 well microtiter plates. For limiting dilutions, a set number of cells in 100 $\mu$l of media were placed in wells in the first row (12 wells) of a microtiter plate in which all wells contained 100 $\mu$l of media, and one half the volume transferred sequentially from one row to the next yielding serial two fold dilutions. Fusion efficiency was calculated as previously described (25). The number of cells seeded into each well in any experiment was based on the maximum number of potential hybrids given a hypothetical 1/1 fusion efficiency. The final volume in each well was 200 to 250 $\mu$l. In selected experiments 10 $\mu$M ouabain in 50 $\mu$l of media with HT was added to yield a 2 $\mu$M ouabain concentration in each well 24 hours after fusion to prevent the growth of normal or transformed cells. A concentration of 2 $\mu$M ouabain was maintained in the wells for 1 week, after which routine feeding was performed. Fusions were fed at 4–7 day intervals by removal of 100-150 $\mu$l of media and replacement with an equal volume of media containing hypoxanthine ($2\times10^{-4}$M) and thymidine ($3.2\times10^{-5}$M) (HT). After selection for expansion, cells were transferred to 24-well multiwells in media containing HT and were maintained in HT until they were passaged once in flasks.

Hybridomas were cloned by resuspension in media containing HT and distributed in microtiter plates such that an average of 1 cell/100 $\mu$l/well was obtained. Cloned cells were fed at weekly intervals with media lacking HT.

In Vitro Immunization and EBV Transformation

PBM from immunized volunteers were transformed to 24-well multiwells in 2.0 ml of media containing 20% FBS and varying concentrations of tetanus toxoid (supplied by Wyeth Laboratories, Philadelphia, Pa.) prepared as previously described (25). As controls, wells were also prepared without additives or with PWM (GIBCO, Grand Island, N.Y.) diluted to a final concentration of 1:1000. Cells were fed initially on day 4 after the start of the culture by removal of 1.8 ml of media and addition of fresh media of the same amount, and thereafter at 4 to 10 day intervals by removal of media and addition of fresh media. EBV transformation was initiated by removal of 1 ml of media from the cultures and addition of 1 ml of a 1:5 dilution of a stock supernatant from the B95-8 cell line collected after the method of Miller et al. (40). Wells to which EBV was added were monitored and fed weekly until continued cell growth and transformation were evident. Growing cultures were transformed to 25 $cm^2$ flasks and expanded for fusion, continued culture and cryopreservation.

Preparation of IgG-1 Human Monoclonal Antibody

Peripheral Blood Mononuclear cells (PBM) from patients with seropositive HIV-1 infection were isolated and transformed by Epstein Barr Virus (EBV) in oligoclonal cultures. One of 915 transformants tested for the production of IgG cell surface reactive antibody to HIV-1 infected HT-H9 cells was found to be positive. This EBV transformant was expanded and fused with the human fusion partner HMMA 2.11TG/O. Of 384 hybridomas screened, 15 (4%) were producing antibody. Two hybridomas were cloned with greater than 80% of tested clones producing the IgG human monoclonal antibody. F 105 human monoclonal antibody is an IgG-1 immunoglobin.

Detection of Antibody and Immunoglobulin Secretion

Supernatants from test wells, or bulk cultures were tested for immunoglobulin secretion using a microelisa assay as previously described (25, 26). In brief, test wells (Immulon 2; Dynatech, Alexandra, Va.) were coated with 100 μl of goat anti-human immunoglobulins (IgM, IgG, and IgA) (Cappell Laboratories, Cochraneville, Pa.) at 30 μgm/ml and incubated for at least 2 hours. Plates were then blocked with PSG with 2.5% FBS (v/v) (PSG 2.5%) for a minimum of two hours, washed twice with phosphate buffered saline (PBS) with 0.05% Tween® 20 (v/v) (PBS-tween) and twice with PBS and 100 μl of test supernatant added. The wells were incubated for 2 hours, washed as above, and 75 μl of peroxidase conjugated goat anti-human immunoglobulins (IgM, IgG and IgA) or specific peroxidase conjugated goat anti-human IgG, IgM or IgA (Tago, Inc., Burlingame, Calif.) diluted 1:3000 in PSG 2.5% were added and incubated for 2 hours. The wells were washed 3 times with PBS-tween and 3 times with PBS after which 100 μl of O-phenylenediamine in citrate buffer were added. Plates were read at 5-45 minutes by observing a color change and scoring from negative to 4+. Antibody to tetanus toxoid was detected using a similar assay except that microelisa plates (Falcon Microtest III Assay Plates; Becton Dickinson, Oxnard, Calif.) were coated with 100 μl of a tetanus toxoid solution at 0.5 μgm/ml (25).

Cell Surface Immunofluorescence

Cell surface phenotypes were determined using both a direct and an indirect immunofluorescence method as previously described (25). In the indirect method, murine monoclonal antibodies specific for IgM, IgG, kappa light chains, lambda light chains, beta-2-microglobulin or Ia were used with a supplied negative control (Coulter, Hialeah, Fla.). Fluorescein conjugated goat anti-mouse immunoglobulins (Tago, Burlingame, Calif.) was used to determine binding of the monoclonal antibodies. In the direct method, fluorescein conjugated goat anti-human IgG, IgM, or IgA (Tago, Inc.) were used with fluorescein conjugated goat anti-mouse immunoglobulins as a negative control. Cell fluorescence was determined using an Epics C cell sorter (Coulter, Hialeah, Fla.).

F 105 Indirect Immunofluorescence

The method by which antigen binding and infectivity was determined as follows. HT-H9 cells may first be exposed to DEAE, or in the alternative, this step may be omitted. Virus, virus diluted with media, or virus diluted with F 105 supernatant and incubated for 30 minutes at 37° C. is mixed with uninfected HT-H9 cells at 0.5 ml/10⁶ cells and allowed to incubate with these cells for 2 hours at 37° C. Following completion of the 37° C. incubation period, the cells are washed with sterile media once, resuspended in PSG, and aliquoted at 1 million cells/sample (for infectivity a sample is set aside for continued growth in regular media). The cells are then centrifuged for 5 minutes at 1,000×g, the supernatant removed and individual samples are mixed with 100 μl of normal serum or HIV+ serum diluted 1:200 or F 105 supernatant undiluted. The cells were then incubated for 30 minutes at 4° C., then washed with PSG (3-4 ml per wash). Fluorescein labeled, (F(AB')₂) goat anti-human IgG antibodies, diluted 1:100, are then added (100 μl/sample) to each of the samples. The samples are then incubated for 30 minutes at 4° C. and washed ×1. The cell pellet is resuspended in ½ ml of PBS and 0.5% formaldehyde incubated for 30 minutes in the cold and then were ready for analysis on the cell sorter.

For infectivity, the cells are cultured and tested on days 4, 7 and 11 for expression of surface viral antigens. The basic immunofluorescence assay is as described above and will detect HIV antigens utilizing either positive sera or F 105 on the surfaces of HT-H9 cells infected with HIV3B.

Quantitation of Antibody or Immunoglobulin Secretion

Spent culture media from flasks containing cloned growing hybridoma cells were collected at 3-4 day intervals, centrifuged at 400 g for 30 minutes, pooled and stored at 4° C. Immunoglobulin was concentrated 5-20 fold by precipitation with saturated ammonium sulfate solution at 50% (v/v). For some experiments, antibody was further concentrated by centrifugation over C50A membrane cones (Amicon Corporation, Danvers, Mass.). Ten microliters of the concentrated antibody, in PBS, were added to the wells of a radial immunodiffusion plate with control reference standards supplied (AccraAssay, ICN Pharmaceuticals, Lisle, Ill.). The plates were evaluated 24-48 hours later. The quantity of immunoglobulin was determined by comparison with standards.

Chromosome Analysis

Karyotypes were studied after preparation using a previously described method (41).

Experimental Results

Construction of Human-Mouse Myeloma Analogs

Bone marrow mononuclear cells were obtained from a patient with an IgA/kappa myeloma and cryopreserved. Prior to the time of aspiration the patient had been heavily treated with numerous chemotherapeutic agents and was uremic and anemic. Eight gm/dl of monoclonal IgA immunoglobulin were present in the serum. After recovery from liquid nitrogen cryopreservation, 25×10⁶ bone marrow mononuclear cells fused with 50×10⁶ murine myeloma cells and were seeded in microtiter wells at 0.25×10⁶ fused cells/well. Ouabain was added to the wells after fusion. Three weeks later 6 out of 96 wells demonstrated hybrid growth and 4 were assayed for immunoglobulin secretion after transfer and further growth in multiwells. Three were found to secrete immunoglobulin. Immunoglobulin secretion was gradually lost over a period of 8 weeks after fusion.

One hybridoma was selected on the basis of quantity and duration of initial secretion and cloned. Two clones from this hybridoma, designated HMMA 2.11 and 2.12 were selected for further evaluation. The derivative cell lines were grown in the presence of increasing concentrations of 6-thioguanine until growth of cells exposed to concentrations of 40 μgm/ml of 6-thioguanine was equal to that of unexposed cell cultures. The cell lines were then grown in the presence of increasing concentrations of ouabain until normal growth was observed at concentration of 50 μm ouabain. The resulting cell lines were sensitive to HAT. One was found to be superior to the other on the basis of fusion efficiency (data not shown) and was evaluated further.

This selected variant was termed HMMA 2.11TG/O and was deposited with the ATCC under Accession Number HB 9583.

The cell line HMMA 2.11TG/O has a doubling time of 20–26 hours. It secretes neither IgG, IgM, nor IgA immunoglobulins detectable by ELISA. The hybrid derivation of the cell line was demonstrated by chromosomal analysis (FIG. 1A) which revealed a mixed murine and human karyotype among the 77–89 (mean 85) chromosomes observed per cell. The cell surface phenotype of the HMMA 2.11TG/O line also confirms the hybrid nature of the cell line (Table I). The HMMA 2.11TG/O cells were found to lack Ia but retain beta-2-microglobulin. Surface IgA, IgM and IgG were absent as were kappa and lambda light chains. The surface phenotype of the original BMMC was strongly IgA and slightly IgM and Ia positive, while negative with IgG. These data indicate that the HMMA 2.11TG/O cell line is a mouse-human hybrid resulting from the fusion of the mouse myeloma P3×63Ag8.653 and cells from human myeloma containing bone marrow.

TABLE II

| | | Results of Fusions With the HMMA 2.11 TG/O Cell line | | | | | |
|---|---|---|---|---|---|---|---|
| Fusion[a] | Source of Cells[b] | Reciprical Fusion Efficiency[c] | Hybride at 15,000 Cells/Well | Wells With Ab or Ig[d] | Successfully Cloned/Cloned | Cloning Efficiency 1 Cell/Well | Ab+ or Ig+ Clones Positive Wells/ Wells Tested |
| HMMA 3.6 | PBM-PWM-I | 20,050 | N.D. | 33 Ig | 3/3 | 20% | 37/91 (40%) Ig |
| F$_3$ | Tet$_1$B$_5$-EBV-I | 5,060 | N.D. | 13 Ab | 1/3 | 29% | 9/63 (14%) Ab |
| F$_5$ | PBM-II | 16,000 | N.D. | 3 Ab | 2/3 | 32% | 6/96 (6%) Ab |
| F$_8$ | Tet$_1$B$_1$-EBV-I | 13,360 | 56/96 | 12 Ab | 1/1 | 29% | 19/44 (43%) Ab |
| F$_{10}$ | Tet$_3$A$_2$-EBV-II | 22,420 | 122/192 | 3 Ab | 1/1 | 11% | 14/27 (52%) Ab |
| F$_{11}$ | Tet$_{3-2}$B$_2$-EBV-II | N.D. | 295/336 | 9 Ab | 2/3 | 27% | 14/51 (27%) Ab[f] |
| F$_{12}$ | Tet$_{3-2}$B$_4$-EBV-II | 25,650 | 117/192 | 1 Ab[e] | N.D. | N.D. | N.D. |

[a]Fusions F$_1$, F$_2$, F$_4$, F$_6$ and F$_7$ were performed with ether cell linen.
[b]PWM = Pekeweed mitogen stimulated, EBV = EBV transformed, TET = invitro immunized, I, II = Volunteer source of cells.
[c]Number of cells fused/hybrid obtained
[d]Ig = Immunoglobulin, Ab = Anti-tetanus Antibody
[e]35 of 45 positive for IgM and 11 of a separate 45 positive for IgG Immunoglobulin secretion.
[f]See Table III

TABLE I

Immunofluorescent Analysis of the Cell Surface Phenotype of HMMA 2.11 TG/O and Donor Bone Marrow Mononuclear Cells

| | Reactivity with cells[a] | |
|---|---|---|
| Antigen | HMMA 2.11 TG/O | BMMC |
| Murine Monoclonal Antibodies | | |
| IA | − | + |
| B-2-M | ++ | N.D.[b] |
| IgG | − | − |
| IgM | − | + |
| Kappa | − | N.D. |
| Lambda | − | N.D. |
| Fluorescein Labeled Goat Antibodies | | |
| Murine IgM + IgG | − | − |
| Human IgM | − | N.D. |
| Human IgG | − | − |
| Human IgA | − | +++ |

[a]− = <20%, + = 20-<50%, ++ = 50-<75%, +++ = 75-100%
[b]N.D. = not done

Production of Human Monoclonal Antibodies and Immunoglobulins

Fusions were performed with the HMMA 2.11TG/O cell line and fresh PBM form normal volunteers. As shown in Table II, fusion with PBM, and PWM stimulated PBM resulted in a relatively high recovery of hybrids. Fusion HMMA 3.6 was performed with PBM stimulated with PWM for 4 days and seeded in a microtiter plate in limiting dilutions from 0.1×10$^6$ cells/well. At 3–4 weeks 43 wells were positive for hybrid growth. The calculated fusion efficiency was 1/20,050 cells. Thirty-three secreted immunoglobulin. Two IgG secreting hybridomas and an IgM secreting hybridoma were cloned from wells seeded at the low dilutions of 25,000, 1562 and 781 cells/well. Only 40% of the clones isolated from these hybridomas were found to secrete immunoglobulins. These data suggest that secretion may be unstable during the initial 4–6 weeks after fusion with PWM stimulated PBM. The clone HMMA3.6 hybridomas continued to secrete immunoglobulin until termination of the cultures 4 months later.

Hybridomas secreting monoclonal antibodies were directly obtainable from an appropriately immunized individual without further stimulation or selection. PBM from a volunteer immunized with tetanus toxoid were obtained seven days after immunization and fused with HMMA 2.11TG/O at a ratio of 2:1. A limiting dilution of fused cells was performed starting with 0.2×10$^6$ cells/well and three additional microtiter plates with 70,000 fused cells/well were initiated. This fusion was termed F5. The resulting fusion efficiency, as shown in Table II, was 1/16,000 fused cells and all wells seeded at a density of 70,000 cells were positive for hybrid growth. From the entire F5 fusion, three wells were found to secrete anti-tetanus IgM antibody and two were cloned. Over 50% of the wells contained anti-tetanus IgG antibodies (data not shown) but none were recovered on transfer to multiwells or cloning in this single experiment.

In order to demonstrate that it is possible to obtain monoclonal antibodies at a late date after in vivo immunization, in vivo immunizations were performed with PBM from donors immunized with tetanus toxoid from 4 to 9 weeks previously. PBM cells were placed in wells of 24 well plates at 1.8–2.5×10$^6$ cells/well, and tetanus toxoid was added to 1 μgm/ml to 0.1 ng/ml. In six experiments with three different individuals anti-tetanus antibody secretion was achieved without further stimulation and was detected by ELISA 8–12 days after the initiation of the cultures. PWM controls were positive for secretion while unstimulated controls were negative (data not shown). Anti-tetanus antibody appeared in wells with various concentrations of tetanus toxoid in different experiments. Duplicate wells stimulated by tetanus toxoid within the range 50–100 ng and 1–5 ng/ml were positive in all the assays.

In five experiments EBV was added to all cultured wells at various times after the start of cultures. Transformation, as determined by increasing cell numbers and ability to expand in flasks was seen in all wells that received EBV on days 8, 12, or 15 after in vitro immunization. Less than 40% of wells showed growth if transformed on days 18 or 21. Anti-tetanus antibody secretion by transformed cells was detected in all wells that were initially positive for anti-tetanus antibody and subsequently transformed on days 12 and 15. An occasional well found to be negative after in vitro immunization became positive 2–3 weeks after EBV transformation on days 12 and 15. Anti-tetanus antibody class was predominantly IgM, with only approximately 20% of antibody secreting wells secreting antibody of the IgG class.

Six separate polyclonal EBV transformed cell lines secreting anti-tetanus antibody from three in vitro immunizations from two individuals were selected for fusion. Generally polyclonal EBV transformed cell lines were allowed to expand such that $7.5-10 \times 10^6$ cells were available, and $5 \times 10^6$ were fused with HMMA 2.11TG/O cell line. Where a fusion efficiency is indicated in Table II, limiting dilutions were performed. Where indicated, the remaining cells were distributed at 15,000 cells/well into additional microtiter plates. Ouabain was added to the fusions 24 hours later. Hybridoma formation was determined 21–28 days after fusion at the time of initial testing for antibody secretion. The average fusion efficiency of HMMA 2.11TG/O with EBV transformed cell lines was 1/16,600 cells. Seventy-two percent of wells seeded with 15,000 fused cells/well had growing hybrids.

Hybridomas initially secreting anti-tetanus antibody were recovered and cloned from 4 to 6 fusions. Fusions F11 and F12 were performed with EBV transformed cell lines secreting both IgG and IgM anti-tetanus antibodies. Cloned anti-tetanus antibody secreting hybridomas were successfully recovered from the F3, F8, F10 and F11 fusions. Of the five separate hybridomas cloned, three secrete IgM antibodies, and two, from the F11 fusion, secrete IgG antibodies. One fusion, F9 (data not shown, limiting dilution lost to contamination), resulted in no recoverable antibody secreting hybrids. Although the EBV transformed cell lines were cryopreserved after fusion, no additional fusions were performed.

To determine the frequency of immunoglobulin secreting hybridomas in fusions with EBV transformed cell lines, hybridomas from the F9 and F12 fusions were screened for IgG and IgM secretion. From the F9 fusion 28 of 32 hybridomas tested secreted IgM, and 1 secreted IgG (91% total secretors). The F12 fusion has 35 of 45 hybridomas secreting IgM (78%) and 11 (24%) of an additional 45 secreting IgG. No attempt was made to recover immunoglobulin secreting clones from these fusions.

Cloning efficiencies of hybridomas from each fusion are shown in Table II and averaged 31%. Cloning was performed 4–6 weeks after fusion. As previously noted, a significant fraction of wells containing clones were negative for antibody secretion. To test the possibility that clones negative for antibody secretion might be secreting immunoglobulin, clones from two hybridomas of the F11 fusion were tested for IgG and IgM secretion. As can be seen from Table III, lack of antibody secretion, in contrast to the HMMA 3.6 fusion, was not a result of the loss of immunoglobulin secretion since 90% of the clones secreted IgG, IgM or both. Nonspecific immunoglobulin secretion by a large fraction of clones may be due to the presence of multiple hybridomas in the primary cultures, or mutational loss of specificity. The secretion of both IgM and IgG in cloned populations is statistically consistent with having seeded two cells in the same wells.

TABLE III

Immunoglobulin and Anti-tetanus Antibody Secretion by Primary Clones From Fusion F11

| Secreted Immunoglobulin or Antibody | Number of Positive Clones | |
|---|---|---|
| | Hybridoma F11DE$_2$* | Hybridoma F11CD$_9$* |
| IgG Antibody | 7 | 6 |
| IgG Immunoglobulin | 14 | 3 |
| IgM Immunoglobulin | 0 | 10 |
| IgG + IgM Immunoglobulins | 0 | 2 |
| None Detected | 2 | 1 |
| Total Screened | 23 | 22 |

*Cells cloned at 0.2 cells/well in 480 wells.

Phenotypic and Chromosomal Analysis

To demonstrate the hybrid derivation of antibody and immunoglobulin secreting hybridomas, the surface phenotype of the parent cell lines and hybridomas were studied and the results are shown in Table I and IV. The EBV transformed B cell lines bear typical cell surface antigens characteristic of the lineage and differentiation associated with these lines (42). At the time of analysis at least two of these cell lines were polyclonal as shown by the presence of both kappa and lambda positive cells. In contrast, the cloned hybrids are shown to lack Ia antigens, and beta-2-microglobulin is variably expressed. The cells from several cloned hybridomas bear monoclonal IgM or IgG and a corresponding single light chain isotype on their surface while several IgG antibody producing cloned hybridomas have absent or reduced surface IgG expression. Interestingly one is positive for IgA heavy chain.

Figure 1B:
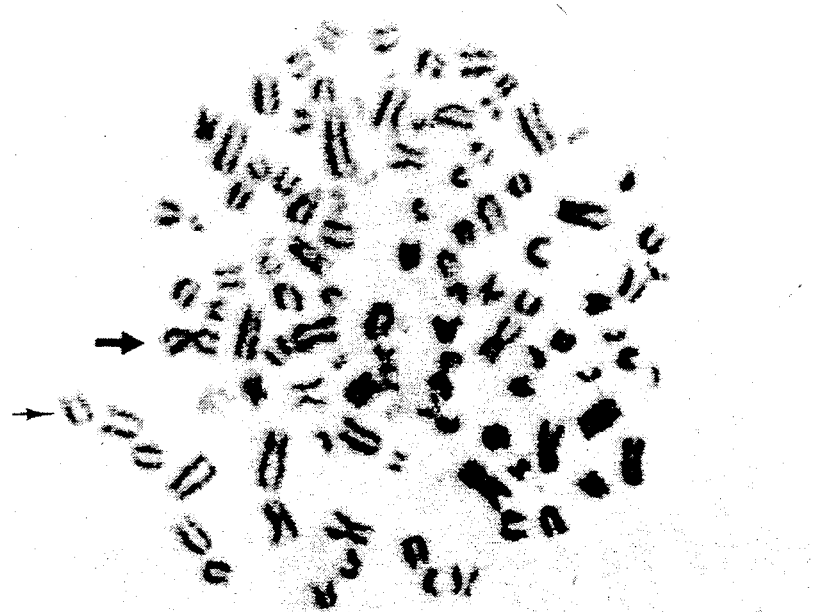
Figure 1C:
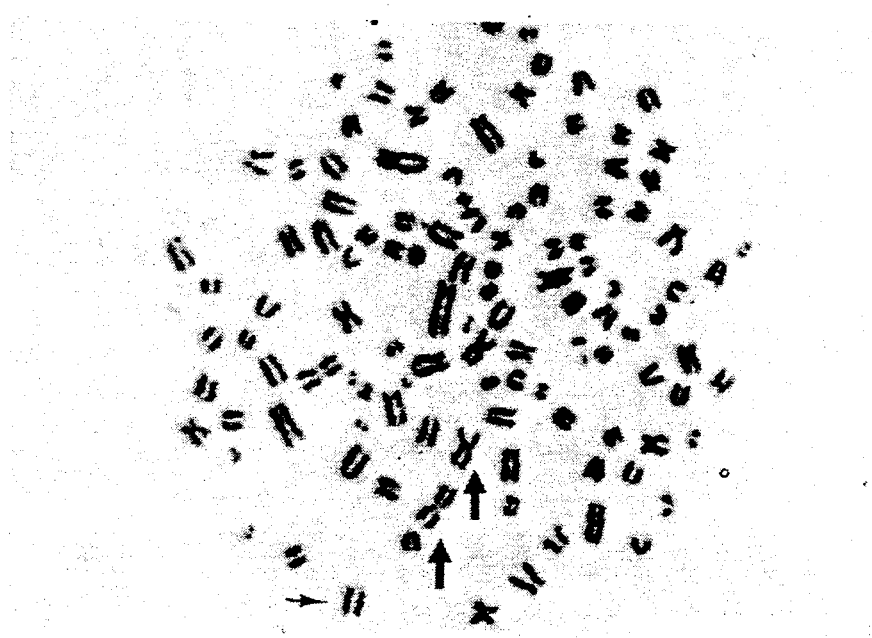

Chromosomal preparations from two of the six cloned hybridomas studies are shown in FIGS. 1B and 1C. Both human and murine chromosomes are clearly present in the preparations. In contrast to the HMMA 2.11TG/O cell line which has 77–89 (mean 85) chromosomes/cell these cloned hybridomas have between 94 and 114 chromosomes/cell (mean 104).

TABLE IV

Immunofluorescent Analysis of the Cell Surface Phenotype of Hybridoma and EBV Transformed Cell Lines

| Antigen | EBV Transformed Cell Lines | | | Cloned Hybridoma Cell Lines | | | | | |
|---|---|---|---|---|---|---|---|---|---|
| | Tet$_{3-2}$B$_5$ | Tet$_{3-2}$B$_2$ | Tet$_1$B$_5$ | F3d$_1$2F$_6$ | F5C$_9$AD$_2$ | F8B$_7$B$_8$ | F11CD$_9$B$_5$ | F11DE$_2$F$_4$ | HMMA 3.61 |
| Murine Monoclonal Antibodies | | | | | | | | | |
| Ia | +++$^a$ | +++ | +++ | − | − | − | − | − | − |
| B-2-M | +++ | +++ | +++ | +++ | ++ | +++ | ++ | +++ | +++ |
| IgG | − | − | − | − | − | − | + | − | ++ |
| IgM | + | + | +++ | + | ++ | + | − | − | − |
| Kappa | − | + | +++ | + | − | + | − | − | ++ |
| Lambda | + | + | ++ | − | + | − | − | − | − |
| Fluorescein Labeled Goat Antibodies | | | | | | | | | |

TABLE IV-continued

Immunofluorescent Analysis of the Cell Surface Phenotype of Hybridoma and EBV Transformed Cell Lines

| Antigen | EBV Transformed Cell Lines | | | Cloned Hybridoma Cell Lines | | | | | |
|---|---|---|---|---|---|---|---|---|---|
| | Tet$_{3-2}$B$_5$ | Tet$_{3-2}$B$_2$ | Tet$_1$B$_5$ | F3d$_{12}$F$_6$ | F5C$_9$AD$_2$ | F8B$_7$B$_8$ | F11CD$_9$B$_5$ | F11DE$_2$F$_4$ | HMMA 3.61 |
| Murine IgG, IgM | − | ND$^b$ | ND | − | − | − | − | − | ND |
| Human IgM | + | ND | ND | +++ | +++ | +++ | − | − | ND |
| Human IgG | − | ND | ND | − | − | − | + | − | ND |
| Human IgA | − | ND | ND | − | − | + | − | − | ND |

$^a$− = <20%, + = 20−<50%, ++ = 50−<75%, +++ = 75−100%
$^b$N.D. = not done

Quantity, Duration, and Stability of Antibody Secretions

Antibody secretion was determined from cultures routinely kept in the laboratory. Spent media from cultures of cloned hybridoma cell lines were collected at 3 to 4 day intervals and pooled. Cells were generally allowed to grow from $0.1 \times 10^6$ to $0.5 \times 10^6$ cells/ml. Supernatants were concentrated 10–20 fold and quantity was determined by radial immunodiffusion. All concentrates were tested for reactivity with tetanus toxoid by ELISA and were found to be reactive at titers of 1:40,000 or greater compared to 1:1500 for unconcentrated spent media. Hybridomas produced 8–42 μgm/ml of IgM (mean 22 μgm/ml) and 21–24 μgms/ml (mean 22 μgm/ml) of IgG under these conditions (Table V).

TABLE V

Antibody Secretion by Hybridomas and Subclones

| Cloned Hybridoma | Antibody Class | Quantity Secreted (ugm/ml)$^a$ | Subclones Secreting Antibody$^c$ |
|---|---|---|---|
| F8B$_7$B$_8$ | IgM | 17 | 42% |
| F8B$_7$C$_{12}$ | IgM | N.D.$^b$ | 50% |
| F3D$_{12}$F$_6$ | IgM | 42 | 83% |
| F5B$_6$A$_6$ | IgM | 21 | 100% |
| F5C$_9$AD$_2$ | IgM | 23 | 50% |
| F10CE$_7$BF$_9$ | IgM | 8 | 100% |
| F11CD$_9$B$_5$ | IgG | 21 | 95% |
| F11DE$_2$F$_4$ | IgG | 22 | 80% |

$^a$Secretion by HMMA 3.6119 = 24 ugm/ml IgG
$^b$Not Done
$^c$% of wells positive for antibody, cloned at 1 cell/well Cloned hybridomas have continued to secrete monoclonal antibody or monoclonal immunoglobulin for periods of 5–10 months after the original cloning. At the present time, no continuously carried culture has lost antibody or immunoglobulin secretion after the initial cloning. Recloning of antibody-secreting hybrids revealed a broad range of stability of secretion. Cloned hybridomas were recloned 4–12 weeks after the initial cloning and tested for anti-tetanus antibody secretion. As can be seen in Table V, 40–100% of new clones were secreting antibody when tested.

The F 105 Monoclonal Antibody

Figure 2A:
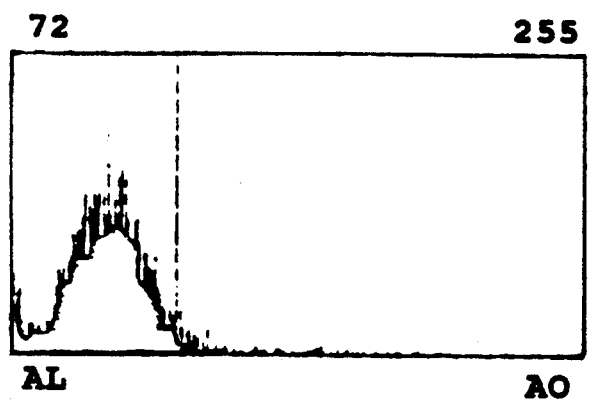
FIGS. 2A, 2B, and 2C: Shows the results of indirect immunofluorescence of the F 105 human monoclonal antibody, as compared to normal serum diluted 1:100, (7%)(2A); serum from an HIV-1 infected patient HIV 24, diluted 1:100 (85%)(2B); and the F 105 monoclonal antibody (54%)(2C).
Figure 2B:
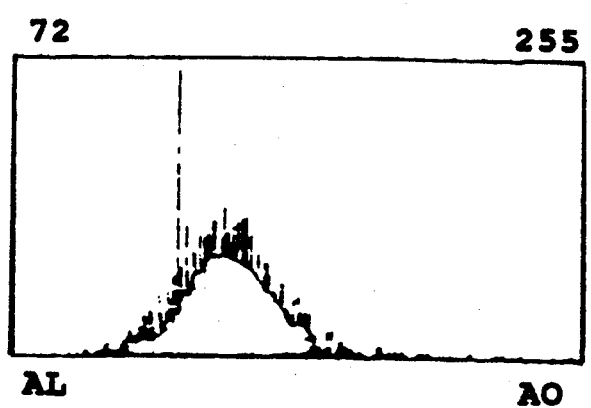
Figure 2C:
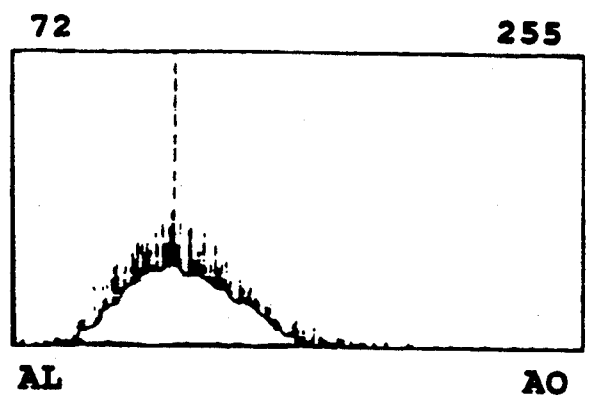

The results of indirect immunofluorescence are shown in FIG. 2. FIG. 2A shows the reactivity of normal serum (diluted 1:100) with HIV3B infected HT-H9 cells. Approximately 7% is considered a negative result. FIG. 2B shows the reactivity of sera from patient HIV 24 (diluted 1:100). Eighty-five percent (85%) of the cells are reactive with this sera. FIG. 2C represents the results with one of several uncloned 105 hybridomas. The F 105 supernatant labels 54% of the cells. Because an IgG specific F(AB')$_2$ goat antihuman FITC was used, this represents IgG antibodies.

F 105 reacts in a dot blot ELISA with HIV virus from supernatants of the HT-H9/HIV 3B infected cells. F 105 did not react with HIV-1 proteins on a commercial Western blot kit.

Table VI shows that F 105 blocks the binding and infection of DEAE primed HT-H9 cells by HIV. The F 105 antigen was not detected on HT-H9 cells after acute exposure to infectious virus but is detected within several days post infection.

TABLE VI

| VIRUS | F105 | CELLS | AB/SERA | IF(1)* | 1B |
|---|---|---|---|---|---|
| − | − | HT-H9 | NS | 21 ± 13 | 21 |
| | | | HIV24 | 19 ± 11 | 23 |
| | | | F105 | 11 ± 9 | 16 |
| + | − | HT-H9 | NS | 20 ± 12 | 21 |
| | | | HIV24 | 50 ± 10 | 93 |
| | | | F105 | 11 ± 10 | 79 |
| + | + | HT-H9 | NS | 25 ± 16 | 28 |
| | | | HIV24 | 26 ± 12 | 33 |
| | | | F105 | 12 ± 12 | 21 |
| − | − | HIV$_{3B}$ | NS | 12 ± 12 | |
| | | | HIV24 | 85 ± 19 | |
| | | | F105 | 63 ± 28 | |

*The results are expressed as per cent fluorescent cells using a goat-anti-human IgG F(AB')$_2$ FITC labelled sera to develop the reaction.
HTH9 cells were exposed to DEAE and then to media, virus, or virus premixed with antibody. Exposure was for 0.5-2 hours and then tested for reactivity with NS or HIV24 serum (1:50) or F105 supernatant (neat). HIV$_{3B}$ was tested simultaneously. 1B represents the results with cells exposed in experiment 1 and tested 4 days after experiment 1. Experiments are being redone with fresh sera, mouse Ig blocking, and shorter incubation times to reduce background.

In a second series of experiments, the results of which are set forth in Table VII below, it is shown that F 105 inhibits the binding of HIV-1 to HT-H9 cells.

TABLE VII

F105 INHIBITS THE BINDING OF HIV-1 TO HT-H9 CELLS

| VIRUS | F105 | CELLS | AB/SERA | IF(1)* | IF(2) | IF(3) | IF(4) |
|---|---|---|---|---|---|---|---|
| − | − | HT-H9 | MS | 10 ± 3 | — | — | 4 |
| | | | HIVPS | 10 ± 2 | — | — | 3 |
| | | | F105 | 9 ± 3 | — | — | 3 |
| + | − | HT-H9 | MS | 7 ± 2 | 4 | 10 | 7 |
| | | | HIVPS | 41 ± 2 | 5 | 13 | 42 |
| | | | F105 | 7 ± 2** | 4 | — | 28 |
| + | + | HT-H9 | MS | 7 ± 1 | 4 | 13 | 5 |
| | | | HIVPS | 9 ± 2 | 4 | 10 | 18 |
| | | | F105 | — | — | — | 9 |
| − | − | HT-H9-HIV$_{3B}$ | MS | 8 ± 2 | 14 | 7 | 7 |

TABLE VII-continued

| F105 INHIBITS THE BINDING OF HIV-1 TO HT-H9 CELLS | | | | | | |
|---|---|---|---|---|---|---|
| VIRUS | F105 | CELLS | AB/SERA | IF(1)* | IF(2) | IF(3) | IF(4) |
| | | | HIVPS | 55 ± 23 | 59 | 59 | 67 |
| | | | F105 | 42 ± 19 | 54 | 43 | 48 |

*IF(1) Immediate IF after viral binding. Viral supernatant and F105 or media were mixed 1:1 and incubated for 30 minutes and then added to cells for 2 hours. These are the average of 3-4 experiments with standard deviations. IF(2), IF(3), and IF(4) refer to cell assays performed 3-4 days, 6-7 days, and 10-11 days after infection respectively and are the average of 2 experiments.

**F105 is negative immediately after viral binding, see additional data. HIVPS and NS are sera from HIV positive patients and normal volunteers respectively. Sera are used at a 1:200 dilution.

The human monoclonal antibody F 105 reacts with a conformationally determined epitope on HIV-1 virions to prevent viral binding and infection. (See FIGS. 3 and 4.)

Experimental Discussion

The present invention provides a method for the construction of a human-mouse myeloma analog for the production of human monoclonal antibodies. The human-mouse myeloma analog was constructed by fusion of bone marrow mononuclear cells from a patient with IgA myeloma and a non-secreting variant, P3×63Ag8.653, of the mouse myeloma cell line MOPC21 (39). The nonsecreting, cloned, mutant hybridoma, HMMA 2.11TG/O is resistant to 6-thioguanine and ouabain and sensitive to HAT. The cell line, HMMA 2.11TG/O, has a high fusion efficiency with peripheral blood mononuclear cells, Pokeweed Mitogen stimulated peripheral blood mononuclear cells, and EBV transformed B cell lines. The cloning efficiency of the second generation hybridomas is high and does not require the presence of feeder cells. Seven separate hybridomas from five fusions secreting anti-tetanus monoclonal antibodies were cloned. Five of these are of the IgM class and two are of the IgG class. Antibody and immunoglobulin secretion is stable and secretion has been maintained for 5-10 months without recloning. Secretion of both classes of antibody is greater than 8 $\mu$gm/ml and as high as 42 $\mu$gm/ml in routine culture. Chromosomal analysis reveals a hybrid karyotype in both the HMMA 2.11TG/O cell line and subsequent second generation hybridoma.

In the present invention, the cell line P3×63Ag8.653 was used as the murine fusion partner because it was a non-producing derivative of MOPC21, and is a cell line of proven efficacy in the production of murine monoclonal antibodies (39). As the human fusion partner, it was reasoned that the most differentiated cell available would be found among the bone marrow cells from a patient with multiple myeloma. Moreover, an IgA myeloma was chosen so that, should the analog secrete immunoglobulin, it would be readily distinguishable from the more desirable IgG and IgM antibodies. While the original fusion gave results consistent with those of other researchers performing human-mouse fusions, e.g. low fusion efficiency and rapid loss of secretion, the resulting non-secreting hybrid cell line has phenotypic characteristics of both the murine and human parental cells and fuses much more readily with human B cells. Moreover, the secretion of human immunoglobulin and antibody by the resulting second generation hybrids is consistent with that seen by murine myeloma cell lines and hybrids (43). Thus, the fusion of the murine myeloma cells with human cells derived from a patient with myeloma has resulted in a human-mouse myeloma analog with human fusion characteristics similar to those seen in murine monoclonal antibody methods.

Since the second important feature of the murine monoclonal antibody technology is the ready availability of large numbers of antibody-producing B cells after programmed immunization, it is important that the HMMA 2.11TG/O cell line be able to fuse with PBM cells from an appropriately immunized donor and readily give rise to antibody secreting hybridomas that are recoverable as cloned secreting cell lines without special selection techniques (47). Nonetheless, many antibodies to specific antigens of interest may not be as readily obtainable, either because in vivo immunization has occurred at some remote, or nonoptimal time in the past, or is not feasible. Thus, it is important to be able to stimulate and expand the antibody-secreting B cell population for fusion (21). In vitro immunization has been successfully used for the production of a secondary immune response to tetanus (48), viral antigens (15, 21), and parasite antigens (49), among others. Numerous polyclonal antibody-secreting EBV transformed B cell lines have been obtained by transformation of peripheral blood, draining lymph nodes, and in vitro immunized B cells (21). The experimental data set forth hereinabove demonstrates that it is possible to immunize routinely in vitro, EBV transform, and expand antibody-producing B cells which can subsequently be fused with the HMMA 2.11TG/O cell line with a high likelihood of recovery of clonable antibody-producing hybrids. Thus, fusions can be performed with already available EBV transformed B lymphoblastoid cell lines secreting known antibody, PBM from optimally immunized volunteers or patients, stimulated PBM, or in vitro immunized and EBV transformed cells.

The data reported herein demonstrate that the human-mouse myeloma analog, HMMA 2.11TG/O, is a superior fusion partner for the production of human monoclonal antibodies. Antibody-producing hybridomas can be recovered after fusion with B cells both directly from peripheral blood and EBV transformed polyclonal cell lines. This cell line should be valuable in the study of a variety of human diseases.

References

1. Kohler, G., Milstein, C., 1975, Continuous Cultures of Fused Cells Secreting Antibody of Predefined Specificity, Nature, 256:495.
2. Steinitz, M., Izak, G., Cohen, S., Ehrenfeld, M., Flechner, I., 1980, Continuous Production of Monoclonal Rheumatoid Factor by EBV-Transformed Lymphocytes, 1980, Nature, 287:443.
3. Sasaki, T., Endo, F., Mikami, M., Sekiguchi, Y., Tada, K., Ono, Y., Ishida, N., Yoshinage, K., 1984, Establishment of Human Monoclonal Anti-DNA Antibody Producing Cell Lines, J. Immunol. Meth., 72:157.

4. Gaskin, F., Kingsley, B., Fu, S. M., 1987, Autoantibodies to Neurofibrillary Tangles and Brain Tissue in Alzheimer's Disease: Establishment of Epstein-Barr Virus Transformed Antibody-Producing Cell Lines, J. Exp. Med., 165:245.

5. Eisenbarth, G. S., Linnenbach, A., Jackson, R., Scearce, R., Croce, C. M., 1982, Human Hybridomas Secreting Anti-Islet Autoantibodies, Nature, 300:264.

6. Satoch, J., Prabhaker, B. S., Haspel, M. V. Ginsberg-Fellner, F., Notkins, A. L., 1983, Human Monoclonal Autoàntibodies that React with Multiple Endocrine Organs, N. Engl. J. Med., 309:217.

7. Valente, W. A., Vitti, P., Yavin, Z., Yavin, E., Rotella, C. M., Grollman, E. F., Toccafondi, R. S., Kohn, L. D., 1982, Monoclonal Antibodies to the Thyrotropin Receptor: Stimulating and Blocking Antibodies Derived from the Lymphocytes of Patients with Graves Disease, Proc. Natl. Acad. Sci. (USA), 79:6680.

8. Alpert, S. D., Turek, P. J., Foung, S. K. H., Engleman, E. G., 1987, Human Monclonal Anti-T Cell Antibody from a Patient with Juvenile Rheumatoid Arthritis, J. Immunol., 138:104.

9. Wunderlich, D., Teramoto, Y. A., Alford, C., Schlom, J., 1981, The Use of Lymphocytes from Auxillary Lymph Nodes of Mastertomy Patients to Generate Human Monoclonal Antibodies, Eur. J. Cancer, 17:719.

10. Watson, D. B., Burns, G. F., Mackay, I. R., 1983, In vitro Growth of B Lymphocytes Infiltrating Human Melanoma Tissue by Transformation with EBV: Evidence for Secretion of Anti-Melanoma Antibodies by Some Transformed Cells, J. Immunol., 130:2442.

11. Irie, R. F., Sze, L. L., Saxton, R. E., 1982, Human Antibody to OFA-I, a Tumor Antigen, Produced In vitro by Epstein-Barr Virus-Transformed Human B-Lymphoid Cell Lines, Proc. Natl. Acad. Sci. (USA), 79:5666.

12. Andreasen, R. B., Olsson, L., 1986, Antibody-Producing Human-Human Hybridomas; III. Derivation and Characterization of Two Antibodies with Specificity for Human Myeloid Cells, J. Immunol., 137:1083.

13. Shoenfeld, Y., Ammon, H., Tal, R., Smordinsky, N. I., Lavie, G., Mor, C., Schteren, S., Mammon, Z., Pinkhas, J., Keydar, T., 1987, Human Monoclonal Antibodies Derived from Lymph Nodes of a Patient with Breast Carcinoma React with MuMTV Polypeptides, Cancer, 59:43.

14. Sikora, K., Alderson, T., Ellis, J., Phillips. J., Watson, J., 1983, Human Hybridomas from Patients with Malignant Disease, Br. J. Cancer, 47:135.

15. Crawford, D. H., Callard, R. E., Muggeridge, M. I., Mitchell, D. M., Zenders, E. D., Beverley, P. C. L., 1983, Production of Human Monoclonal Antibody to X31 Influenza Virus Nucleoprotein, J. Gen. Virol., 64:697.

16. Zurawski, V. R., Spedden, S. E., Black, P. H., Haber, E., 1978, Clones of Human Lymphoblastoid Cell Lines Producing Antibody to Tetanus Toxoid, Curr. Top. Microbial. Immunol., 81:152.

17. Rosen, A., Persson, K., Klein, G., 1983, Human Monoclonal Antibodies to a Genus-Specific Chlamydia Antigen, Produced by EBV-Transformed B Cells, J. Immunol., 130:2899.

18. Gigliotti, F., Insel, R. A., 1982, Protective Human Hybridoma Antibody to Tetanus Toxin, J. Clin. Invest., 70:1306.

19. Croce, C. M., Linnenbach, A., Hall, W., Steplewski, Z., Koprowski, H., 1980, Production of Human Hybridomas Secreting Antibodies to Measles Virus, Nature, 288:488.

20. Larrick, J. W., Truitt, K. E., Raubitschek, A. A., Senyk, G., Wang, J. C. N., 1983, Characterization of Human Hybridomas Secreting Antibody to Tetanus Toxoid, Proc. Natl. Acad. Sci. (USA), 80:6376.

21. Crawford, D. H., 1986, Use of Virus to Prepare Human-Derived Monoclonal Antibodies, In: The Epstein-Barr Virus Recent Advances, Ed: Epstein, M. A. Achong, B. G., John Wiley and Sons, New York, 251.

22. Kabat, E. A., Nickerson, K. G., Liao, J. Grossbard, L., Osserman, E. F., Glickman, E., Chess, L., Robbins, J. B., Schneerson, R., Yang, Y., 1986, A Human Monoclonal Macroglobulin with Specificity for a(-2–8)-Linked Poly-N-Acetyl-Neuraminic Acid, The Capsular Polysaccharide of Group B Meningococci and Escherichia Coli K1, which Crossreacts with Polynucleotides and with Denatured DNA, J. Exp. Med., 164:642.

23. Olsson, L., Kronstrom, H., Cambon-De Mouzon, A., Honsik, C., Jakobsen, B., 1983, Antibody Producing Human-Human Hybridomas, I. Technical Aspects, J. Immunol. Meth., 61:17.

24. Schwaber, J., Cohen, E. P., 1973, Human X Mouse Somatic Cell Hybrid Clone Secreting Immunoglobulins of Both Patental Types, Nature, 244:444.

25. Posner, M. R., Schlossman, S. F., Lazarus, H., 1983, Novel Approach to the Construction of Human "Myeloma Analogues" for the Production of Human Monoclonal Antibodies, Hybridoma, 2:369.

26. Schwaber, J. F., Posner, M. R., Schlossman, S. F., Lazarus, H., 1984, Human-Human Hybrids Secreting Pneumococcal Antibodies, Human Immunol,. 9:137.

27. Potter, M. O., 1972, Immunoglobulin-Producing Tumors and Myeloma Proteins of Mice, Physiol. Rev., 52:631.

28. Horibata, K., Harris, A. W., 1970, Mouse Myelomas and Lymphomas in Culture, Exp. Cell Res. 60:61.

29. Casali, P., Inghirami, G., Nakamurta, M., Davies, T. F., Notkins, A. L., 1986, Human Monoclonals from Antigen-Specific Selection of B Lymphocytes and Transformation by EBV, Science, 234:476.

30. Steinitz, M., Koskimies, S., Klein, G., Makela, O., 1978, Establishment of Specific Antibody Producing Human Lines by Antigen Preselection and EBV-Transformation, Curr. Top. Microbiol. Immunol., 81:156.

31. Cote, R. J., Morrissey, D. M., Houghton, A. N., Beattie, E. J., Oettgen, H. F., Old, L. J., 1983, Generation of Human Monoclonal Antibodies Reactive with Cellular Antigens, Proc. Natl. Acad. Sci. (USA), 80:2026.

32. Brodin, T., Olsson, L., Sjorgren, H., 1983, Cloning of Human Hybridoma, Myeloma, and Lymphoma Cell Lines Using Enriched Human Monocytes as Feeder Layer, J. Immunol. Meth., 60:1.

33. Glassy, M. C., Handley, H. H., Hagiwara, H., Royston, I., 1983, UC 729-6, A Human Lympholastoid B-Cell Line Useful for Generating Antibody-Secreting Human-Human Hybridomas, Proc. Natl. Acad. Sci. (USA), 80:6327.

34. Teng, N. N. H., Lam, K. S., Riera, F. C., Kaplan, H. S., 1983, Construction and Testing of Mouse-Human Heteromyelomas for Human Monoclonal Antibody Production, Proc. Natl. Acad. Sci. (USA), 80:7308.

35. Fuong, S. K. H., Perkins, S., Raubitschek, A., Larrick, J., Lizak, G., Fishwild, D., Engleman, E. G., Grumet, F. C., 1984, Rescue of Human Monoclonal Antibody Production from an EBV-Transformed B Cell Line by Fusion with a Human-Mouse Hybridoma, J. Immunol. Meth., 70:83.
36. Carroll, W. L., Thielmans, K., Dilley, J., Levy, R., 1986, Mouse X Human Heterohybridomas As Fusion Partners with Human B Cell Tumors, J. Immunol. Meth., 89:61.
37. Ostberg. L., Pursch, E., 1983, Human X (Mouse X Human) Hybridomas Stably Producing Human Antibodies, Hybridomas, 2:361.
38. Stevens, R. H., Macy, E., Morrow, C., Saxon, A., 1979, Characterization of a Circulating Subpopulation of Spontaneous Antitetanus Toxoid Antibody Producing B Cells Following in Vivo Booster Immunization, J. Immunol., 122:2498.
39. Kearney, J. F., Radbruch, A., Liesgang, B., Rajewsky, K., 1979, A New Mouse Myeloma Cell Line that has Lost Immunoglobulin Expression but Permits the Construction of Antibody-Secreting Hybrid Cell Lines, J. Immunol, 123:1548.
40. Miller, G., Lipman, M., 1973, Release of Infectious Epstein-Barr Virus by transformed Marmoset Leukocytes, Proc. Natl. Acad. Sci. (USA), 70:190.
41. Weitberg, A. B., Weitzman, S. A., Destrempes, M., Latt, S. A., Stossel, T. P., 1983, Stimulated Human Phagocytes Produce Cytoogenetic Changes in Cultured Mammalian Cells, New Eng. J. Med., 308:26.
42. Halper, J., Fu, S. M., Wang, C. Y., Winchester, R., Kunkel, H. G., 1978, Patterns of Expression of Human "Ia-Like" Antigens During the Terminal Stages of B Cell Development, J. Immunol., 120:1480.
43. Laskov, R., Kim, K. J., Asofsky, 1979, Induction of Amplified Synthesis and Secretion of IgM by Fusion of Murine B Lymphoma with Myeloma Cells, Proc. Natl. Acad. Sci. (USA), 76:915.
44. Laskov, R., Kim, J. K., Kanellpoulos-Langevin, C., Asofsky, R., 1980, Extinction of B-Cell Surface Differentiation Markers in Hybrids Between Murine B-Lymphoma and Myeloma Cells, Cell Immunol., 55:251.
45. Riley, S. C., Brock, E. J., Kuehl, W. M., 1981, Induction of Light Chain Expression in a Pre-B Cell Line by Fusion to Myeloma Cells, Nature, 289:804.
46. Hamano, T., Kim, K. J., Lieserson, W. M., Asofsky, R., 1982, Establishment of a B Cell Hybridoma with B Cell Surface Antigens, J. Immunol., 129:1403.
47. Posner, M. R., Berkman, R., Fife, J., Lazarus, H., 1984, Optimal Conditions for Obtaining Human Monoclonal Antibodies After Immunization with Tetanus, Clin. Res., 32:355A.
48. Volkman, D. J., Allyn, S. P., Fauci, A. S., 1982, Antigen-Induced In vitro Antibody Production in Humans: Tetanus Toxoid-Specific Antibody Synthesis. J. Immunol., 129:107.
49. Nutman, T. B., Withers, A. S., Ottesen, E. A., 1985, In Vitro Parasite Antigen-Induced Antibody Responses in Human Helminth Infections, J. Immunol., 135:2794.
50. Ollson, L., Andreasen, R. B., Osta, A., Christensen, B., Biberfield, P., 1984, J. Exp. Med., 159:537.
51. Nadler, L. M., Stasherko, P., Hardy, R., Pesando, J. M., Yunis, E. J., Schlossman, S. F., 1981, Human Immunology, 1:77.
52. Koprowski, H., Steplewski, Z., Heryln, D., Herlyn, M., 1978, Proc. Natl. Acad. Sci., 75:3405.
53. Dippold, W. G., Lloyd, K. O., Li LTC, et al., 1980, Proc. Natl. Acad. Sci., 77:6114.
54. Morgan, A. C., Galloway, D. R., Reisfield, R. A., 1981, Hybridoma, 1:27.
55. Brown, J. P., Woodburn, R. G., Hart, C. E., Hellstrom, I., Hellstrom, K. E., 1981, Natl. Acad. Sci., 78:539.
56. Muller, M., Zotter, S., Kemme, C., 1976, J. Nat. Cancer Inst., 56:295.
57. Tamana, M., Kajdos, A. H., Niedermeir, W., Durkin, W. J., Mestecky, J., 1981, Cancer, 47:2696.
58. Shoenfeld, Y., Schwartz, R. S., 1984, New Engl. J. Med., 311:1019.
59. Miller, R. A., Maloney, D. G., Levy, R. A., 1982, N. Eng. J. Med., 307:687.
60. Larson, S. M., Brown, J. P., Wright, P. W., et al., 1983, J. Nucl. Med., 4:123.
61. Miller, R. A., Maloney, D., Stratte, P., Levy, R., 1983, Hybridoma 2:238.
62. Dillman, R. O., Shawler, D. L., Dillman, J. B., Royston, I., 1984, J. Clin. Oncol., 2:881.
63. Nowinski, R., Berglund, C., Lane, J., et al., 1980, Science, 210:537.
64. Steinitz, M., Klein, G., Koshimies, S., Makel, C., 1977, Nature, 269:420.
65. Lane, H. C., Shelhamer, J., Mostowski, H. S., Fauci, A. S., 1982, J. Exp. Med., 155:333.
66. Melchers, F., Potter, M., Warner, N. L., 1978, Current Top. Microbiol. and Immunol., 8:1X.
67. Houghton, A. N., Brooks, H., Cote, J., et al., 1983, J. Exp. Med., 158:53.
68. Abrams, P. G., Knost, J. A., Clarke, G. Wilburn, S., Oldham, R. K., Foon, K. A., 1983, J. Immunol., 131:1201.
69. Popovic, M., Sarngadharan, M. G., Read E., Gallo R. C., 1984, Detection, Isolation, and Continuous Production of Cytopathic Retroviruses (HTLV-III) form Patients with AIDS and Pre-AIDS. Sci 224:497–500.
70. Kanki, P. J., M'Boup, S., Ricard, D., Barin, F., Denis, F., Boye, C., Sangare, L., Travers, K., Albaum, M., Marlink, R., Romet-Lemmonne, J. L., Essex, M., 1987, Human T-Lymphotropic Virus Type 4 and the Human Immunodeficiency Virus in West Africa, Sci. 236:827–831.
71. Kaminsky, L. S., McHugh, T., Stites, D., Volberding, P., Henle G., Henle, W., Levy, J. A., 1985, High Prevalence of Antibodies to Acquired Immune Deficiency Syndrome (AIDS)-Associated Retrovirus (ARV) in AIDS and Related Conditions But Not in Other Disease States, P.N.A.S., 82:5535-5539.
72. Gallo, R. C., Salahuddin, S. Z., Popovic, M., Shearer, G. M., Kaplan, M., Haynes, B. F., Palker, T. J., Redfield, R., Oleske, J., Safai, B., White, G., Foster, P., Markham, P. D., 1984, Frequent Detection and Isolation of Cytopathic Retroviruses (HTLV-III) from Patients with AIDS and at Risk for AIDS, Sci. 224:500-503.
73. Clavel, F., et al., 1986, Isolation of a New Human Retrovirus from West African Patients with AIDS. Sci. 233:343-346.
74. Mayer, K. H., et al., 1987, Correlation of Enzyme-Linked Immunoabsorbent Assays for Serum Human Immunodeficiency Virus Antigen and Antibodies To Recombinant Viral Proteins with Subsequent Clinical Outcomes in a Cohort of Asymptomatic Homosexual Men, Am. J. Med. 83:208–212.
75. McDougal, J. S., et al. 1987, Antibody Response to Human Immunodeficiency Virus in Homosexual Men, J. Clin, Inves. 80:316–324.
76. Zagury, D., et al,, 1986, Long-Term Cultures of HTLV-III-Infected T Cells: A Model of Cytopathology of T Cell Depletion in AIDS, Sci. 231:850–853.
77. Sattentau, Q. J., et al., 1986, Epitopes of the CD4 Antigen and HIV Infection, Sci. 234:1120–1123.
78. Chanh, T. C., et al., 1987, Monoclonal Anti-Idiotypic Antibody Mimics the CD4 Receptor and Binds Human Immunodeficiency Virus, P.N.A.S. 84:3891–3895.
79. McDougal, J. S., et al., 1986, Binding of the Human Retrovirus HTLV-III/LAV/ARC/HIV to the CD4 (T4) Molecule: Conformation Dependence, Epitope Mapping, Antibody Inhibition, and Potential for Idiotypic Mimicry, M. Immuno. 137:2937–2944.
80. Lane, H. C., et al., 1983, Abnormalities of B-Cell Activation and Immunoregulation in Patients with the Acquired Immunodeficiency Syndrome, N. Eng. J. Med., 309:453–458.
81. Zanetti, A. R., et al., 1986, Hepatitis B Vaccination of 113 Hemophiliacs: Lower Antibody Response in Anti-LAV/HTLV-III-Positive Patients, Am. J. Hemoto. 23:339–345.
82. Yarchoan, R., et al., 1986, Mechanisms of B Cell Activation in Patients with Acquired Immunodeficiency Syndrome and Related Disorders, J. Clin. Inves., 78:439–447.
83. Martinez-Maza, O., et al., 1987, Infection with the Human Immunodeficiency Virus (HIV) is Associated with An In Vivo Increase In B Lymphocyte Activation and Immaturity, J. Immuno. 138:3720–3724.
84. Aman, P., et al., 1984, Epstein-Barr Virus Susceptibility of Normal Human B Lymphocyte Populations, J. Exp. Med., 159:208–220.
85. Robert-Guroff, M., et al., 1987, HTLV-III Neutralizing Antibody Development in Transfusion-Dependent Seropositive Patients with B-Thalassemia, J. Immuno. 138:3731–3736.
86. Robert-Guroff, M., et al., 1985, HTLV-III-Neutralizing Antibodies in Patients with AIDS and AIDS-Related Complex, Nature 316:72–74.
87. Anderson, K. C., et al., 1986, Transfusion-Acquired Human Immunodeficiency Virus Infection Among Immunocompromised Persons, Ann. Int. Med. 105:519–527.
88. Groopman, J. E., et al., 1987, Characterization of Serum Neutralization Response to the Human Immunodeficiency Virus (HIV), Aids Res. Hum. Retroviruses 3:71–85.
89. Weiss, R. A., 1985, Neutralization of Human T-Lymphotropic Virus Type III by Sera of AIDS and AIDS-Risk Patients, Nature 316:69–71.
90. Laurence, J., et al., 1987, Characterization and Transcriptase Activity, Sci. 235:1501–1504.
91. Lifson, J. D., 1986, Induction of CD4-Dependent Cell Fusion by the HTLV-III/LAV Envelope Glycoprotein, Nature 323:725–728.
92. Hahn, B. H., et al., 1986, Genetic Variation in HTLV-III/LAV Over Time in Patients with AIDS or at Risk for AIDS, Sci. 232:1548–1553.
93. Robert-Guroff, M., 1986, In Vitro Generation of an HTLV-III Variant by Neutralizing Antibody, J. Immuno. 137:3306–3309.
94. Wong-Staal, F., et al., 1985, Genomic Diversity of Human T-Lymphotropic Virus Type III (HTLV-III) Sci. 229:759–762.
95. Ho, D. D., et al., 1987, Human Immunodeficiency Virus Neutralizing Antibodies Recognize Several Conserved Domains on the Envelope Glycoproteins, J. Virol. 61:2024–2028.
96. Cronin, W., et al., 1985, Anti-Lymphocyte Antibodies in Patients with Acquired Immune Deficiency Syndrome (AIDS), Firs Int. Aids Mtg., Atlanta.
97. Kiprov, D. D., et al., 1985, Correlation of Antilymphocyte Antibodies (ALA) with Seropositivity of Lymphadenopathy Virus (LAV). Firs Int. Aids Mtg., Atlanta.
98. Lowder, J. N., et al., 1987, Suppression of Anti-Mouse Immunoglobulin Antibodies in Subhuman Primates Receiving Murine Monoclonal Antibodies Against T Cell Antigens, J. Immuno. 138:401–406.
99. Monroe, J. G., et al., 1986, Anti-Idiotypic Antibodies and Disease, Immuno. Inves. 15:263–286.
100. Wasserman, N. H. et al., 1982, P.N.A.S. 79:4810–4814.
101. Cleveland, W. L. et al., 1983, Nature, 305:56–57.

What is claimed:
1. A hybridoma deposited with the ATCC under Accession No. HB10363 and designated F 105.
2. The human monoclonal antibody produced by the hybridoma of claim 1 and designated F 105.
3. The human monoclonal antibody of claim 2 labelled with a detectable marker.
4. The human monoclonal antibody of claim 2 conjugated with a cytotoxic agent.

* * * * *